United States Patent
Laufer et al.

(10) Patent No.: US 8,882,789 B2
(45) Date of Patent: *Nov. 11, 2014

(54) METHODS AND SYSTEMS FOR TISSUE MANIPULATION

(75) Inventors: Michael Laufer, Menlo Park, CA (US); Thomas Bromander, Andover, MA (US); Amos Cruz, Franklin, MA (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 707 days.

This patent is subject to a terminal disclaimer.

(21) Appl. No.: 11/867,574

(22) Filed: Oct. 4, 2007

(65) Prior Publication Data

US 2009/0018389 A1 Jan. 15, 2009

Related U.S. Application Data

(60) Provisional application No. 60/849,414, filed on Oct. 4, 2006.

(51) Int. Cl.
*A61B 17/08* (2006.01)
*A61B 17/04* (2006.01)
*A61N 5/10* (2006.01)
*A61B 17/00* (2006.01)
*A61F 5/00* (2006.01)

(52) U.S. Cl.
CPC ..... *A61B 17/0401* (2013.01); *A61B 2017/0496* (2013.01); *A61B 17/0469* (2013.01); *A61B 2017/0472* (2013.01); *A61N 5/1001* (2013.01); *A61B 2017/00827* (2013.01); *A61B 2017/0417* (2013.01); *A61B 2017/00004* (2013.01); *A61B 2017/0404* (2013.01); *A61B 2017/00867* (2013.01); *A61F 5/0083* (2013.01); *A61B 17/00234* (2013.01)
USPC .......................................... 606/153; 606/151

(58) Field of Classification Search
USPC ......... 606/139, 151, 153, 232, 157, 220, 192; 607/37, 126, 149; 128/898
See application file for complete search history.

(56) References Cited

U.S. PATENT DOCUMENTS

| | | | |
|---|---|---|---|
| 4,969,892 A | 11/1990 | Burton et al. |
| 5,556,428 A | 9/1996 | Shah |
| 5,616,131 A | 4/1997 | Sauer et al. |
| 5,618,270 A | 4/1997 | Orejola |
| 5,649,960 A | 7/1997 | Pavletic |
| 5,861,003 A | 1/1999 | Latson et al. |
| 5,893,856 A | 4/1999 | Jacob et al. |

(Continued)

FOREIGN PATENT DOCUMENTS

| | | |
|---|---|---|
| WO | WO-03094785 A1 | 11/2003 |
| WO | WO-2005020802 A2 | 3/2005 |

OTHER PUBLICATIONS

International Preliminary Report on Patentability (Application No. PCT/US06/046026) dated May 19, 2009.

(Continued)

*Primary Examiner* — Tuan V Nguyen
(74) *Attorney, Agent, or Firm* — William C. Geary, III

(57) ABSTRACT

Endoscopic treatment methods and systems for endoscopic treatment are provided. An endoluminal treatment device and method in an exemplary embodiment includes introducing an endoluminal device into a lumen of a patient and engaging a wall of the lumen with an implant device without creating an incision in the patient. The implant device can be a drug delivery device or medical device.

5 Claims, 19 Drawing Sheets

(56) References Cited

U.S. PATENT DOCUMENTS

| | | | |
|---|---|---|---|
| 5,944,738 A | 8/1999 | Amplatz et al. | |
| 6,120,525 A | 9/2000 | Westcott | |
| 6,152,935 A | 11/2000 | Kammerer et al. | |
| 6,352,503 B1 | 3/2002 | Matsui et al. | |
| 6,375,671 B1 | 4/2002 | Kobayashi et al. | |
| 6,461,293 B1 | 10/2002 | Forsell | |
| 6,470,892 B1 | 10/2002 | Forsell | |
| 6,494,888 B1 | 12/2002 | Laufer et al. | |
| 6,506,196 B1 | 1/2003 | Laufer | |
| 6,520,974 B2 | 2/2003 | Tanner et al. | |
| 6,663,639 B1 | 12/2003 | Laufer et al. | |
| 6,746,460 B2 | 6/2004 | Gannoe et al. | |
| 6,773,441 B1 | 8/2004 | Laufer et al. | |
| 6,821,285 B2 | 11/2004 | Laufer et al. | |
| 6,835,200 B2 | 12/2004 | Laufer et al. | |
| 7,037,344 B2 | 5/2006 | Kagan et al. | |
| 7,083,630 B2* | 8/2006 | DeVries et al. | 606/153 |
| 7,267,679 B2 | 9/2007 | McGuckin, Jr. et al. | |
| 7,361,185 B2 | 4/2008 | O'Malley et al. | |
| 7,431,725 B2* | 10/2008 | Stack et al. | 606/151 |
| 7,455,681 B2 | 11/2008 | Wilke et al. | |
| 7,520,884 B2 | 4/2009 | Swanstrom et al. | |
| 7,566,298 B2 | 7/2009 | Nicholson, IV | |
| 7,621,925 B2 | 11/2009 | Saadat et al. | |
| 7,686,829 B2 | 3/2010 | Elliott et al. | |
| 7,691,112 B2 | 4/2010 | Chanduszko et al. | |
| 2002/0035361 A1 | 3/2002 | Houser et al. | |
| 2002/0138086 A1 | 9/2002 | Sixto et al. | |
| 2002/0183768 A1 | 12/2002 | Deem et al. | |
| 2002/0193816 A1 | 12/2002 | Laufer et al. | |
| 2003/0018358 A1 | 1/2003 | Saadat | |
| 2003/0093117 A1 | 5/2003 | Saadat | |
| 2003/0144695 A1 | 7/2003 | McGuckin et al. | |
| 2003/0164304 A1 | 9/2003 | Imran et al. | |
| 2003/0191495 A1 | 10/2003 | Ryan et al. | |
| 2003/0216754 A1 | 11/2003 | Kraemer et al. | |
| 2004/0010245 A1 | 1/2004 | Cerier et al. | |
| 2004/0034371 A1 | 2/2004 | Lehman et al. | |
| 2004/0044364 A1 | 3/2004 | DeVries et al. | |
| 2004/0087976 A1* | 5/2004 | DeVries et al. | 606/142 |
| 2004/0092892 A1 | 5/2004 | Kagan et al. | |
| 2004/0093091 A1 | 5/2004 | Gannoe et al. | |
| 2004/0107004 A1 | 6/2004 | Levine et al. | |
| 2004/0116992 A1 | 6/2004 | Wardle et al. | |
| 2004/0122456 A1 | 6/2004 | Saadat et al. | |
| 2004/0147958 A1 | 7/2004 | Lam et al. | |
| 2004/0148021 A1 | 7/2004 | Cartledge et al. | |
| 2004/0152947 A1 | 8/2004 | Schroeder et al. | |
| 2004/0158125 A1 | 8/2004 | Aznoian et al. | |
| 2004/0193117 A1 | 9/2004 | Laufer et al. | |
| 2004/0193184 A1 | 9/2004 | Laufer et al. | |
| 2004/0193190 A1* | 9/2004 | Liddicoat et al. | 606/153 |
| 2004/0193193 A1 | 9/2004 | Laufer et al. | |
| 2004/0193194 A1 | 9/2004 | Laufer et al. | |
| 2004/0194790 A1 | 10/2004 | Laufer et al. | |
| 2004/0220596 A1 | 11/2004 | Frazier et al. | |
| 2004/0220637 A1 | 11/2004 | Zdeblick et al. | |
| 2004/0225304 A1 | 11/2004 | Vidlund et al. | |
| 2004/0225305 A1* | 11/2004 | Ewers et al. | 606/153 |
| 2004/0243211 A1 | 12/2004 | Colliou et al. | |
| 2005/0033328 A1 | 2/2005 | Laufer et al. | |
| 2005/0059984 A1 | 3/2005 | Chanduszko et al. | |
| 2005/0065571 A1 | 3/2005 | Imran | |
| 2005/0065601 A1 | 3/2005 | Lee et al. | |
| 2005/0080444 A1 | 4/2005 | Kraemer et al. | |
| 2005/0090873 A1 | 4/2005 | Imran | |
| 2005/0096673 A1 | 5/2005 | Stack et al. | |
| 2005/0143760 A1 | 6/2005 | Imran | |
| 2005/0177180 A1 | 8/2005 | Kaganov et al. | |
| 2005/0192599 A1 | 9/2005 | Demarais | |
| 2005/0192601 A1 | 9/2005 | Demarais | |
| 2005/0203500 A1* | 9/2005 | Saadat et al. | 606/27 |
| 2005/0228415 A1 | 10/2005 | Gertner | |
| 2005/0251157 A1 | 11/2005 | Saadat et al. | |
| 2005/0251160 A1 | 11/2005 | Saadat et al. | |
| 2005/0251165 A1 | 11/2005 | Vaughan et al. | |
| 2005/0251208 A1 | 11/2005 | Elmer et al. | |
| 2005/0261713 A1 | 11/2005 | Hassan et al. | |
| 2005/0267406 A1 | 12/2005 | Hassler | |
| 2005/0267533 A1 | 12/2005 | Gertner | |
| 2006/0020276 A1 | 1/2006 | Saadat et al. | |
| 2006/0020277 A1 | 1/2006 | Gostout et al. | |
| 2006/0074458 A1 | 4/2006 | Imran | |
| 2006/0089571 A1 | 4/2006 | Gertner | |
| 2006/0142790 A1 | 6/2006 | Gertner | |
| 2006/0155327 A1 | 7/2006 | Briganti et al. | |
| 2006/0157067 A1 | 7/2006 | Saadat et al. | |
| 2006/0161185 A1 | 7/2006 | Saadat et al. | |
| 2006/0178550 A1 | 8/2006 | Jenson | |
| 2006/0183975 A1 | 8/2006 | Saadat et al. | |
| 2008/0243144 A1 | 10/2008 | Laufer et al. | |
| 2008/0312729 A1 | 12/2008 | Laufer et al. | |
| 2008/0312750 A1 | 12/2008 | Laufer et al. | |
| 2009/0018558 A1 | 1/2009 | Laufer et al. | |
| 2009/0018594 A1 | 1/2009 | Laufer et al. | |

OTHER PUBLICATIONS

International Preliminary Report on Patentability (Application No. PCT/US07/080485) dated Apr. 23, 2009.

International Search Report (Application No. PCT/US07/80485) dated Jun. 5, 2008.

DeMarco et al. "Outcomes of endoluminal gastric plication for the treatment of gastroesophageal reflux disease" BUMC Proceedings 2003; 16:392-393.

Olympus, "Your Vision, Our Future Medical Endoscope & Surgical Products" pp. 1-5, dated Jan. 9, 2006, downloaded Jun. 5, 2008, <http://web.archive.org/web/20060109095625/http://www.olympus.co.jp/en/mesg/endoscope/Gastroenterology/Endo-Therepy/etp/rfb/rfb_01.cfm>.

Olympus, "Your Vision, Our Future Medical Endoscope & Surgical Products" pp. 1-5, downloaded Jun. 5, 2008, <http://olympus.co.jp/en/mesg/endoscope/Gastroenterology/Endo-Therepy/etp/rfb/rfb_01.cfm>.

European Search Report for EP App. No. 10180976.2 dated Oct. 21, 2010.

* cited by examiner

METHODS AND SYSTEMS FOR TISSUE MANIPULATION

CROSS-REFERENCE TO RELATED APPLICATION

This application claims the benefit of Provisional Patent Application No. 60/849,414, filed Oct. 4, 2006, which is incorporated by reference herein in its entirety.

TECHNICAL FIELD OF THE INVENTION

Generally, the present invention is related to endoluminal surgical devices, methods, device, and drug delivery. More particularly, the devices and methods provide for endoluminal gastric restriction, endoluminal gastric tissue reconfiguration, endoluminal drug delivery, endoluminal device delivery, and the like.

BACKGROUND OF THE FIELD OF THE INVENTION

Laparoscopic surgery has greatly reduced the size and scope of incisions made in a patient and resulted in reduced morbidity and mortality rates. However, even with the reductions in the size and scope of incisions as a result of laparoscopic surgery, complications in and during surgical procedures remain. A technique that is developing to further reduce surgical complications is to work through an endoluminal access port. One endoluminal access port is the mouth and this access port can give a surgeon access to a patient's esophagus and stomach.

Stomach tissue often needs surgical treatment to treat fistulas and to close transgastric incisions to stop stomach fluids from leaking from the stomach to surrounding tissue and to stop infectious matter from spreading from or to the stomach tissue. Other stomach treatments include stomach reduction procedures for obese patients. Traditionally, physicians have been placing devices such as the Lap Band® on the external surface of the gastric wall to create a restricted stomach capacity. Another traditional procedure for stomach reduction includes a laparoscopic procedure in which surgeons protrude into the stomach from the exterior of the patient and staple the stomach into a smaller volume. This restriction creates a pouch inside the stomach which fills quickly when food is ingested and assists in generating a sensation of being full. However, these procedures have drawbacks such as complications from port punctures of the stomach, large incisions, substantial recovery time, expense, lost productive work time, infection, and the like.

However, the incision required by the current surgical procedures include a morbidity and mortality rate that can be reduced by reducing or eliminating the need for an incision by approaching the surgical site through endoluminal procedures.

SUMMARY OF THE INVENTION

According to an embodiment, the present invention includes an implant device including a medical implant configured to be implanted into a lumen of a body without creating an incision in the body, wherein the medical implant is configured to maintain a plication in a wall of the lumen and wherein the medical implant includes a medical treatment. The medical treatment can include a drug delivery, a time released drug delivery, a coating, a biological stimulation device, a monitoring device, a feeding tube, a bioresorbable material, and combinations thereof. The biological stimulation device can be selected from the group consisting of an electrical stimulation device, mechanical stimulation device, vibratory device, sound device, ultra-sound device, chemical stimulatory device, neuro-transmitter stimulation device, thermal stimulation, sensory stimulatory device, and combinations thereof.

In some embodiments, the implant device further includes a controller configured to control the biological stimulation device. The controller can control the biological stimulation device from external to the body and through radio frequency. The monitoring device can be selected from the group of a pH sensor, pressure sensor, video sensor, chemical sensor, hormone sensor, dilation sensor, fluid sensor, ion sensor, tissue extension sensor, and combinations thereof. In some embodiments, the medical treatment includes material selected from radioactive material, chemotherapy material, biological material, and combinations thereof.

In some embodiments, the medical treatment is configured to treat a gastric condition. In some embodiments, the medical implant is includes bioresorbable material including a drug.

In alternative embodiments, an endoscopic treatment method includes introducing an endoscopic device into a lumen of a patient without creating an incision in the patient, engaging a wall of the lumen with an end effecter of the endoscopic device to form a plication, and activating the end effecter to secure the plication with an anchor object and a treatment device, wherein the treatment device is coupled with the anchor object.

In some embodiments, an endoscopic treatment method includes introducing an endoscopic device into a lumen of a patient without creating an incision in the patient, introducing a treatment device into the lumen, engaging a wall of the lumen with an end effecter of the endoscopic device, forming a first plication in the wall of the lumen, forming a second plication in the wall of the lumen adjacent the first plication, and coupling the first plication with the second plication to thereby form a first double plication wherein an open pocket is formed between the first plication and the second plication. In alternative embodiments, the method includes forming a second double plication adjacent the first double plication, wherein a second open pocket formed by the second double plication and the open pocked formed by the first double plication are axially aligned. In other embodiments, the method includes forming an artificial biological tube by aligning multiple double plications such that open pockets formed by the multiple double plications axially align. In some embodiments, the method includes coupling the first double plication with the second double plication.

According to yet other embodiments, an endoscopic GERD treatment method includes introducing an endoscopic device into a lumen of a patient without creating an incision in the patient, engaging a wall of the lumen with an end effecter of the endoscopic device, and forming a plication in the wall of the lumen near the gastro-esophageal-junction such that an artificial biologic tube is formed distal to the gastro-esophageal-junction to block gastric fluid from interfering with tissue of the esophagus. In some embodiments, the method includes forming a plurality of plications extending distally from the gastro-esophageal-junction. In some embodiments, the artificial biologic tube is between about 0.5 cm and about 5 cm in length. In alternative embodiments, the artificial biologic tube is between about 0.5 cm and about 3 cm in diameter. In further embodiments, the plurality of plications is coupled together with glue, suture, wire, or tissue re-growth after stimulation.

In other embodiments, an endoscopic obesity treatment method includes introducing an endoscopic device into a stomach of a patient without creating an incision in the patient, engaging a wall of the stomach with an end effector of the endoscopic device, and forming a plication in the wall of the stomach such that an artificial biologic tube is formed within the stomach of the patient and thereby reducing a volume of the stomach to treat obesity.

In alternative embodiments, a medical implant apparatus includes an anchor object configured to couple with tissue and an adjustable mechanism configured to interact with the anchor object such as to apply alternative forces upon the anchor object in response to a stimulus. In some embodiments, the adjustable mechanism is coupled with the anchor object through suture material. In other embodiments, the adjustable mechanism is coupled with the anchor object through surgical wire. In some embodiments, the adjustable mechanism shortens in response to a stimuli. In some embodiments, the adjustable mechanism includes a mechanism selected from the group consisting of: piezoelectric, magnetic, screw-threads, spring, memory metal, elastic, mechanical mechanism, temperature sensitive material, and combinations thereof. According to some embodiments, the stimuli is selected from the group of a radio frequency, ultra-sound, mechanical force, pressure, direct mechanical manipulation, magnetic force, chemical interaction, enzyme interaction, fluid, temperature, biological fluid, cellular interaction, cellular by-product, inter-cellular constituent, intra-cellular constituent, food, digestion by-product, a lapse of time, and combinations thereof. In some embodiments, the device further includes a plurality of anchor objects wherein each anchor object is coupled with the adjustable mechanism such that an adjustable substantially sphincter shaped tissue structure is formed.

According to some embodiments, a method for temporary tissue restructuring includes implanting an anchor object onto tissue to be adjustably restructured, associating an adjustable mechanism with the anchor object such that a force generated by the adjustable mechanism can change a relative position of the anchor object with respect to the adjustable mechanism and thereby restructures tissue, and stimulating the adjustable mechanism to generate the force. In some embodiments, the method further includes a plurality of anchor objects, wherein each anchor object is coupled with the adjustable mechanism. The plurality of anchor objects can be coupled in series with the adjustable mechanism. In some embodiments, the method includes shortening the adjustable mechanism in response to a stimuli and thereby resulting in a distance between the adjustable mechanism and the anchor object reducing such as to tighten tissue between the anchor object and the adjustable mechanism. In other embodiments, the adjustable mechanism includes a mechanism selected from the group of: piezoelectric, magnetic, screw-threads, spring, memory metal, elastic, mechanical mechanism, temperature sensitive material, and combinations thereof. In some embodiments, the stimulating is selected from a radio frequency, ultra-sound, mechanical force, pressure, direct mechanical manipulation, magnetic force, chemical interaction, enzyme interaction, fluid, temperature, biological fluid, cellular interaction, cellular by-product, inter-cellular constituent, intra-cellular constituent, food, digestion by-product, a lapse of time, and combinations thereof.

According to alternative embodiments, the present invention discloses a surgical tool support system that includes an anchor object configured and dimensioned to be attached to a body tissue and a manipulation line extending from the anchor object and configured and dimensioned to couple with a surgical tool. In some embodiments, the manipulation line is fabricated from one of the group of a suture, resorbable suture, stainless steel, surgical wire, braided wire, and combinations thereof.

In alternative embodiments, the present invention also includes a method of manipulating a surgical tool including forming an incision in body tissue, attaching a manipulation line to body tissue near the incision, introducing a surgical device through the incision in the body tissue, attaching a free end of the manipulation line to the surgical device, and manipulating the surgical tool to perform a medical treatment procedure. The manipulation line can provide a cantilever for the surgical tool. The manipulation line at least partially supports the surgical device. In some embodiments, method includes implanting a plurality of manipulation lines between the body tissue and the surgical tool. The plurality of manipulation lines are evenly distributed around the surgical tool.

DETAILED DESCRIPTION OF EMBODIMENTS OF THE INVENTION

Figure 1:
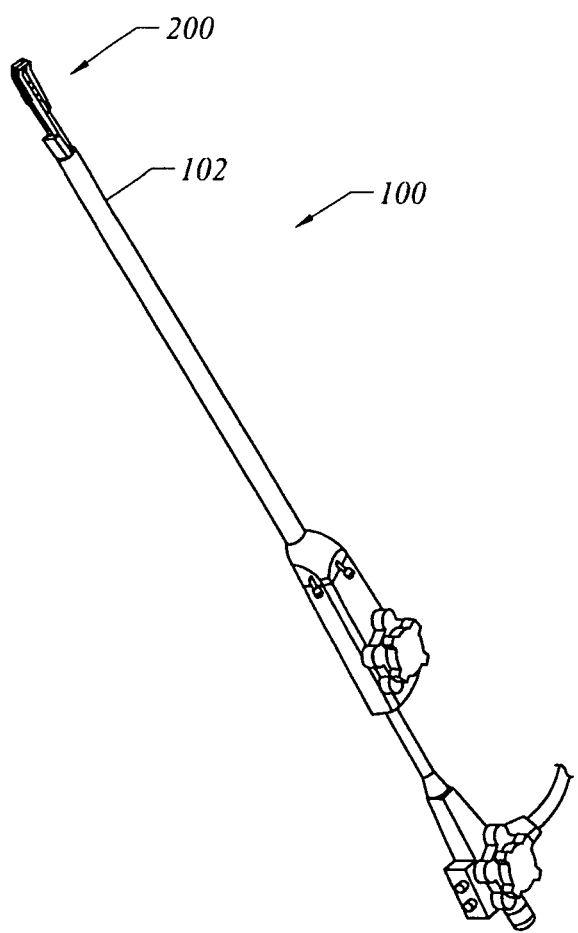
FIG. 1 shows a schematic view of an endoluminal surgical device according to an embodiment of the present invention.

An endoluminal device 100, such as that shown in FIG. 1 and disclosed in U.S. Pat. Nos. 6,835,200; 6,821,285; 6,773, 441; 6,663,639; 6,506,196; and 6,494,888, and U.S. Published Application No's. 2005/0033328; 2004/0194790; 2004/0193194; 2004/0193193; 2004/0193184; 2004/0193117; 2002/0193816; and U.S. Provisional patent application No. 60/741,510 filed Dec. 1, 2005, the disclosure of each being hereby incorporated by reference in their entirety, is utilized in the present invention to manipulate tissue of a patient. Generally, the endoluminal device 100 is configured such that it can be positioned within a hollow organ by entry through a body cavity opening, such as for example, positioning the device into the stomach via the mouth of a patient. Once situated, the device is capable of manipulating tissue and implanting objects or devices.

According to some embodiments of the present invention, methods and devices are provided for delivering devices or drugs into the lumen of an organ, manipulate tissue, close incisions, repair fistulas, and the like by an endoluminal approach. The tissue of an organ, such as for example, the stomach, can be manipulated to generate a fold, plication, or tube and a suture based implant can be implanted to maintain the manipulated character of the tissue. In some embodiments, a drug or device can also be introduced into the lumen of the organ and implanted or attached to the organ wall with a suture based implant. In some embodiments, after the tissue is manipulated into folds or plications the folds can be positioned vertically with respect to each other and the suture based implants can be drawn together such as to form an artificial biological tube.

Figure 2:
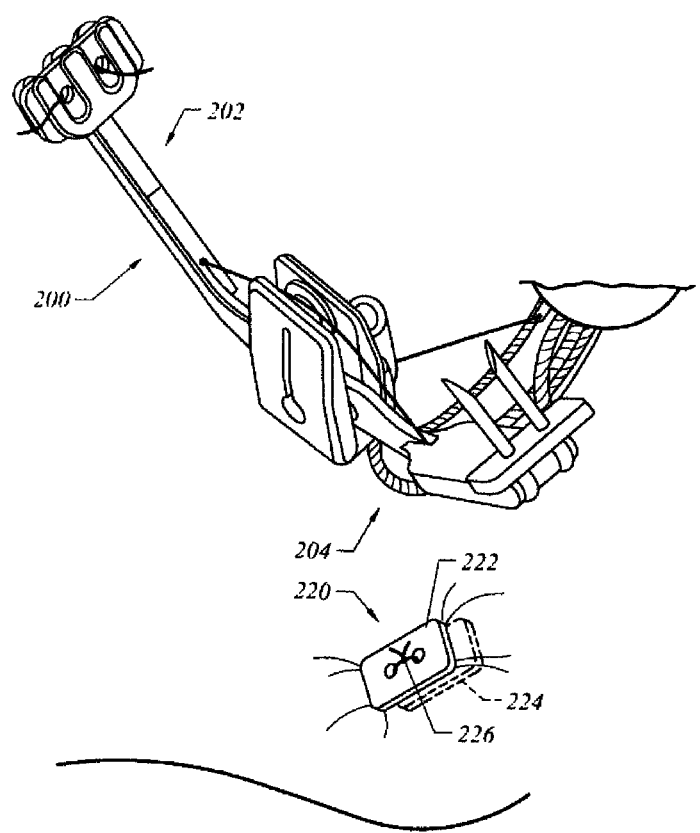
FIG. 2 shows a schematic view of a tissue engaging end effecter of an endoluminal surgical device according to an embodiment of the present invention.

Referring to FIG. 1, endoluminal surgical device 100 is shown according to an embodiment of the present invention. Endoluminal surgical device 100 further includes a generally longitudinal and flexible shaft 102 that includes an end effecter 200 (FIG. 2) configured near its distal end. End effecter 200 includes first arm 202 and second arm 204. First arm 202 and second arm 204 are configured to engage tissue and implant anchor object 220. According to some embodiments, anchor object 220 generally includes pledgets 222 and 224 which, according to some embodiments, are connected by suture 226. Endoluminal surgical device 100, end effecter 200, and anchor object 220 are further disclosed in the reference publications and applications that are incorporated herein by reference. As described in further detail in the publications and applications incorporated herein by reference, anchor object can be constructed from any biocompatible material, such as, but not limited to, stainless steel, cobalt chromium, titanium, alloys of such metals, biocompatible polymers, soluble polymers, non-soluble polymers, swellable polymers, absorbable polymers, suture material, bioresorbable suture, bioabsorbable suture, combinations thereof, or the like.

Figure 3:
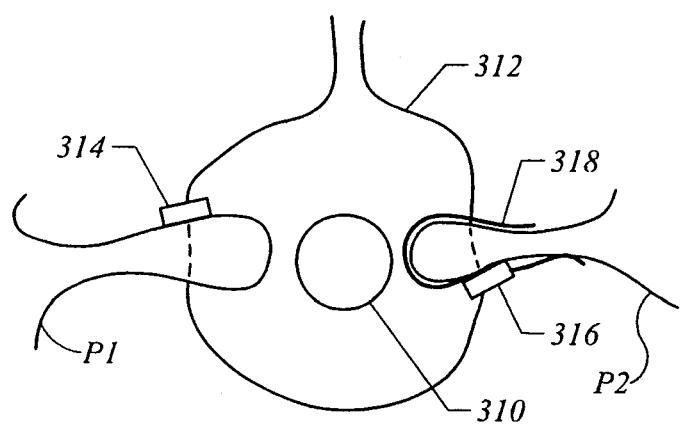
FIG. 3 shows an implanted device according to an embodiment of the present invention.

Referring now to FIG. 3, endoluminal surgical device 100 is utilized to manipulate tissue. Tissue from the wall of a hollow organ, such as for example the stomach, is formed into plications, such as plication P1. Plication P1 is formed by gathering or manipulating tissue of the wall of the organ with end effecter 200 into a fold and piercing the folded tissue with needle of end effecter 200. Needle includes suture 312 and a suture based implant or pledget 314 associated therewith. According to an embodiment, one end of suture 312 is attached to pledget 314 and the other end of suture 312 remains free and outside the patient. According to an alternative embodiment, both ends of suture 312 remain free and outside the patient's body, however, pledget 314 is attached to suture at a predetermined location. Pledget 314 can be loosely attached or securely attached to suture 312 by a knot, a clip, integral with suture 312, combinations thereof, or the like. Following implantation of pledget 314, a second pledget 316 is positioned with respect to suture 312. Second pledget 316 is preferable positioned with respect to suture 312 outside the body, however, second pledget 316 can be positioned onto suture 12 inside the hollow organ. Second pledget 316 is then moved into the hollow organ to be manipulated, a second fold of tissue or plication P2 is formed with the endoluminal or endoscopic surgical device 100 and plication P2 is pierced with needle of the endoscope 100. When plication P2 is pierced, suture 312 is pushed through plication P2, thereby, bringing pledget 316 into position adjacent a side of plication P2. Following positioning of pledgets 314 and 316, suture 312 is tightened such that plication P1 and plication P2 are drawn together. Preferably, pledget 314 and pledget 316 are positioned on opposing sides of plication P1 and P2, respectively. In an alternative embodiment, pledget 314 and pledget 316 are positioned on the same side of plication P1 and plication P2. After suture 312 is tightened such that plication P1 and plication P2 are approximated together, suture 312 is fixed. According to alternative embodiments, suture 312 can be either removably fixed or irremovably fixed to hold plication P1 and plication P2 in position. Suture 312 can be fixed with a knot, a suture clip, fused together, combinations thereof, or the like. Furthermore, a predetermined pressure can be applied through the tightening of suture 312 such as to generate a predetermined treatment condition between the plications. According to some embodiments, this procedure is performed in the stomach of a patient. According to one embodiment of treating a stomach condition, plication P1 and plication P2 are formed approximately 2 cm from gastroesophageal (GE) junction 310. According to alternative embodiments, plication P1 and plication P2 are formed between 2 cm and 5 cm from GE junction 310. Where the stomach condition to be treated requires enhancement or replacement of the gastric valve, such plications are preferably located in cooperative relationship with the GE junction to form an artificial gastric valve.

According to alternative embodiments, pledgets 314 and 316 may or may not be used to form plications P1 and P2, respectively. It should be appreciated that depending on a condition to be treated, tissue type being treated, location of treatment, size or area to be treated, combinations thereof, and the like, pledgets 314 and 316 may not be necessary, thereby, using suture 312 to form plications P1 and P2 and tighten plications P1 and P2 together. In some embodiments, multiple pledgets can be implanted adjacent one another such as to treat a large tissue disturbance, such as a large incision, re-incision, necrotic site, fistula, combinations thereof, or the like.

In some embodiments, a patch 318 can be introduced with endoluminal device 100 into the organ to be treated. Patch 318 can be associated with a tissue engaging portion of the device and placed on the wall of the organ when the tissue engaging portions grasp the wall to form the plication. In some embodiments, patch 318 may be coupled with a plication, such as plication P2, through the securing implant such as pledget 316. In one exemplary embodiment, patch 318 may be formed as a resilient, clip-like member having at least two arms that can be secured to a plication previously formed by manipulating the tissue with the endoluminal device 100. As shown, for example, in FIG. 3, piercing of the tissue is not required for securing such an embodiment. According to alternative embodiments, patch 318 can be attached at a plurality of locations to the wall of the organ. Patch 318 can increase the integrity of the organ. In some embodiments, patch 318 includes therapeutic agents such as, for example, antibiotics, drugs, inhibiting agents, anti-inflammatory agents, combinations thereof, and the like. The therapeutic agents can be coated on patch 318 or they can be dispersed throughout the material that forms patch 318. Patch 318 can also be fabricated from non-absorbable or bio-resorbable materials. Other treatment devices as described below also my be employed.

Figure 4:
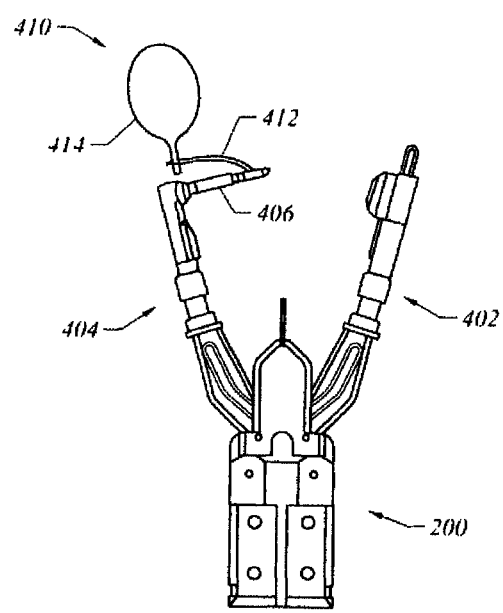
FIG. 4 shows a device positioned on an end effecter prior to implantation according to an embodiment of the present invention.

Referring now to FIG. 4, end effecter 200 is shown having first arm 402 and second arm 404. First arm 402 and second arm 404 are configured to engage and manipulate tissue. In some embodiments, second arm 404 includes a tissue piercing needle 406. In some embodiments, implant device 410 includes suture 412 that is attached to implant 414. In some embodiments implant 414 can be, but is not limited to, a drug delivery device, such as for example a delayed delivery material, delayed absorbable drug eluding material, selectively drug permeable material or membrane, time release delivery device, combination thereof, or the like. In alternative embodiments, implant 414 can be, but is not limited to a stimulator device, such as for example, an electrical stimulation device, mechanical stimulation device, vibratory device, sound stimulation device, ultra-sound stimulation device, combinations thereof, or the like. In some embodiments, the stimulation device can be configured to stimulate a sense of a patient. In a preferred embodiment, the sense stimulated by the stimulation device can be a sense of satiety in the patient such that the patient's desire for eating is subsided. In further alternative embodiments, implant 414 can be, but is not limited to, a sensory device, such as for example, a device to monitor pH, pressure, temperature, salinity, hydration, cellular activity, protein levels, glucose levels, insulin levels, hormone levels, biological function, biological secretion, cellular uptake, cellular secretion, combinations thereof, and the like. In further embodiments, implant 414 can be, but is not limited to, a device to control biological activity, such as for example, inter or intra cellular pH, temperature, salinity, cellular function, cellular excretion, cellular uptake, glucose levels, insulin levels, combinations thereof, and the like. In alternative embodiments, suture 412 can be resorbable suture material or non-resorbable suture material.

In some embodiments, first arm 402 and second arm 404 are positioned with respect to tissue that is to be manipulated. The arms are manipulated by actuating a control on endoluminal surgical device 100. When first arm 402 and second arm 404 are actuated, they move toward each other and tissue positioned between the arms is engaged and pierced with needle 406. In some embodiments, needle 406 is coupled with suture 412, and suture 412 is attached to implant device 410. Following activation of the arms and piercing tissue with needle 406, suture 412 is pierced through the tissue and extends through the tissue with implant device 410 on one side of the pierced tissue and a free end of suture 412 on the other side of the pierced tissue. Alternatively, suture 412 can be formed as a loop to be secured around a natural or formed anatomical feature, such as a plication, utilizing first and second arms 402 and 404 without piercing the tissue.

Figure 5:
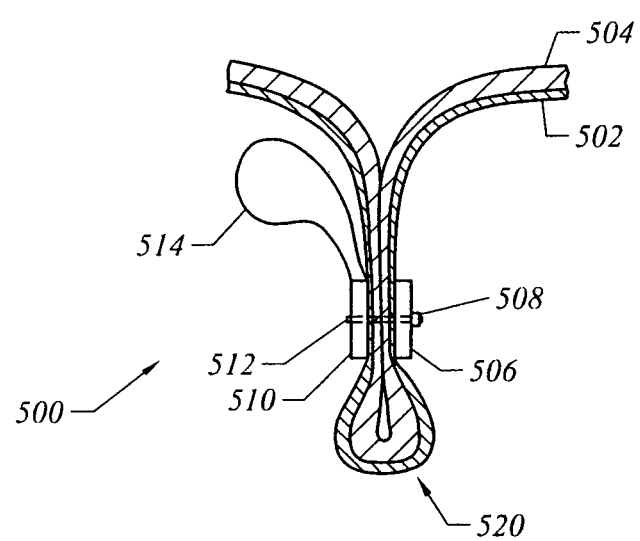
FIG. 5 shows a tissue plication including an implanted device according to an embodiment of the present invention.

According to FIG. 5, implant device 500 is shown implanted with respect to tissue of a patient. According to an embodiment, tissue, such as stomach wall tissue 504 and stomach mucosa 502 are formed into a plication 520. Plication 520 is affixed with an anchor object that includes pledgets 506 and 510. In some embodiments, pledgets 506 and 510 can be coupled together with a tee bar 508 and suture 512 and in other embodiments pledgets can be coupled together only with suture 512. Implant 514 is attached to the anchor object. According to some embodiments, as shown in FIG. 5, implant 514 can be integral with pledget 510, coupled with pledget 510, or removable coupled with pledget 514. In some embodiments, the coupling between pledget 510 and implant 514 can be degradable over a predetermined time such that implant 514 become detached from pledget 510. According to other embodiments, implant 514 can be any of the implant devices, sensors, drugs, drug delivery devices, monitors, control devices, combinations thereof, and the like that are described herein and/or incorporated into this application by reference.

Figure 6:
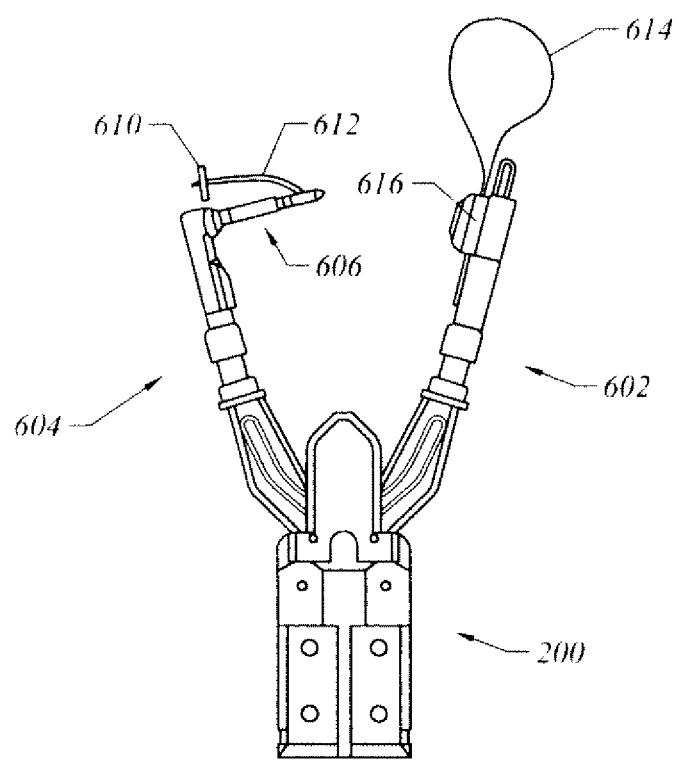
FIG. 6 shows another device positioned on an end effecter prior to implantation according to an embodiment of the present invention.

Referring now to FIG. 6, end effecter 200 is shown having first arm 602 and second arm 604. Second arm is shown having needle 606 for piercing tissue, however, as will be appreciated first arm 602 and second arm 604 and the components associated therewith can be interchanged such that needle 606 could be associated with first arm 602, and the like. Needle 606 is coupled or threaded with suture 612, which includes a pledget 610 associated therewith. As shown in FIG. 6, first arm 602 is configured to couple with implant 614. Implant 614 further includes an affixing portion 616 for engaging with needle 606 and coupling thereto to bind tissue therebetween. In some embodiments, implant 614 can be any of the implant devices described herein or incorporated herein by reference. In other embodiments, suture 612 and pledget 610 can be fabricated according to other embodiments described herein or incorporated herein by reference.

Figure 7:
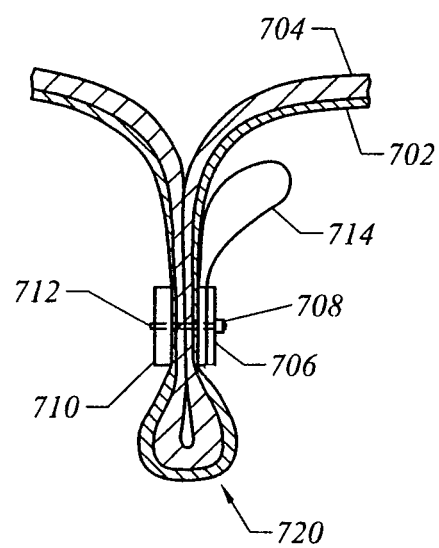
FIG. 7 shows another tissue plication including an implanted device according to an embodiment of the present invention.

According to FIG. 7, a plication 720 can be formed from a tissue wall or lining 704 that may or may not include a mucosa 702. Plication 720 is formed from binding tissue 704 with an anchor object that includes pledgets 706 and 710. In some embodiments, pledgets 706 and 710 can be coupled with suture 712 and tee bar 708. According to some embodiments, implant 714 can be implanted with another object by coupling implant 714 between tissue wall 704 or tissue mucosa 702 and pledget 706.

Figure 8:
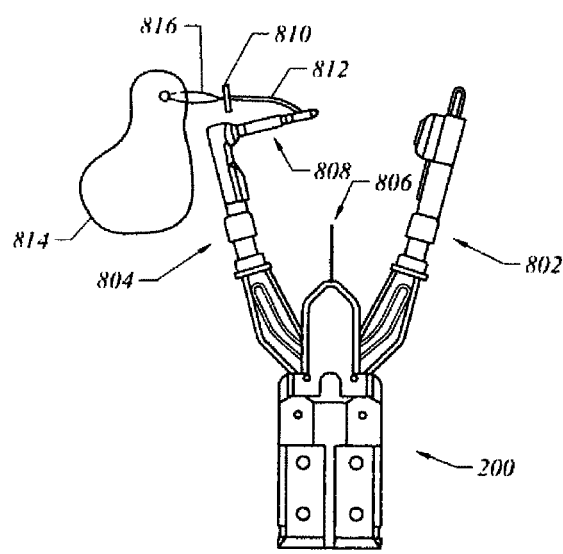
FIG. 8 shows yet device positioned on an end effecter prior to implantation according to an embodiment of the present invention.
Figure 9:
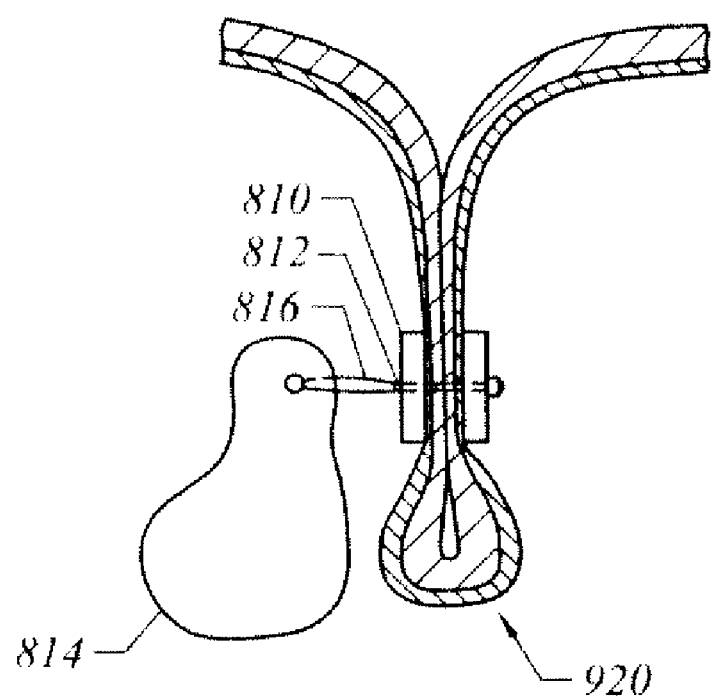
FIG. 9 shows another tissue plication including an implanted device according to an embodiment of the present invention.

According to other embodiments, as shown in FIG. 8, implant 814 can be implanted on a tether such that implant 814 is relatively affixed to tissue but not rigidly affixed to any particular tissue. According to FIG. 8, end effecter 200 includes first arm 802, second arm 804, and tissue retractor 806. Second arm 804 includes tissue piercing needle 808 for piercing tissue and implanting implant 814. Needle 808 further includes suture 812 for affixing tissue that is pierced by needed 808 into a plication. Suture 812 can include pledget 810 for biasing against tissue. In some embodiments, suture 812 extends further beyond pledget 810 and couples with implant 814. In other embodiments, second suture 816 extends from pledget 810 and couples with implant 814. According to such embodiments, implant 814 is implanted into a patient and affixed into a general location, however, implant 814 is semi-free to move within patient to the extent of tether provided between pledget 810 and implant 814. FIG. 9 shows tethered implant 814 in an implanted position with respect to a tissue plication 920. According to some embodiments, plication 920 is formed by anchoring a plication of tissue with an anchor object that includes implant 814 tethered thereto by second suture 816.

Figure 10:
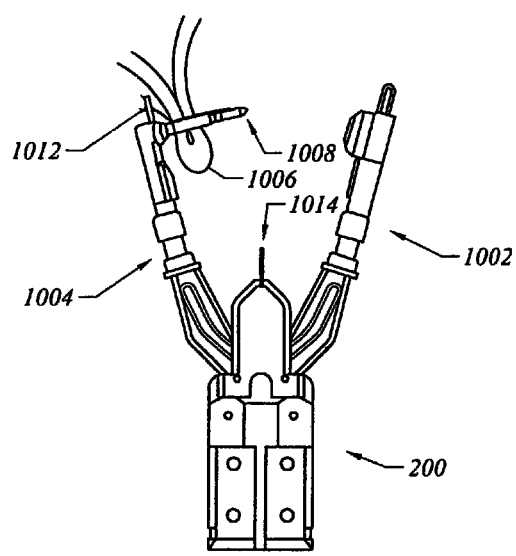
FIG. 10 shows an end effecter with a tissue plication formed on a needle of the end effecter according to an embodiment of the present invention.
Figure 11:
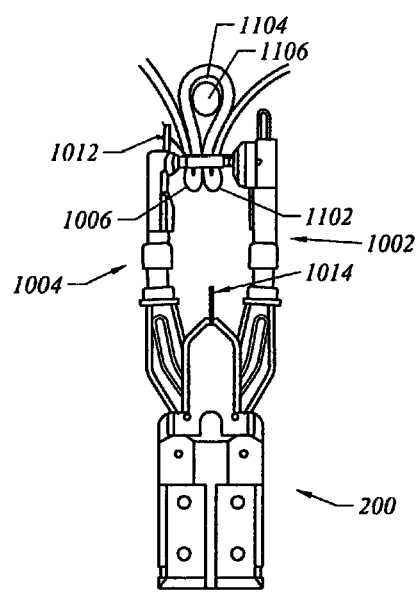
FIG. 11 shows an end effecter with multiple tissue plications formed on a needle of the end effecter according to an embodiment of the present invention.

Referring now to FIGS. 10-12C, a plication that forms an open pocket or biologic tube is shown. In FIG. 10, an end effecter 200 has a first arm 1002, a second arm 1004, and a tissue retractor 1014 and is used to form a tissue plication 1006, as described herein. Plication 1006 is formed by grasping tissue with retractor 1014 and manipulating first arm 1002 and second arm 1004 together such that needle 1008 pierces the tissue. Suture 1012 is associated with needle 1008 such that suture 1012 is pierced through tissue with needle 1008. After piercing the tissue with needle 1008, the tissue is retained on needle 1008. Referring now to FIG. 11, retractor 1014 is used a second time to grasp a second portion of tissue such that the tissue can be positioned with respect to first arm 1002, second arm 1004, and needle 1008 and be pierced with needle 1008 to form second plication 1102. By forming two adjacent plications 1006 and 1102, an open pocket 1104 is formed. In some embodiments, an implant 1106 is housed in open pocket 1104.

In some embodiments, end effecter 200 can have multiple retractors 1014 such that the retractor does not have to be removed from the tissue after forming a first plication in order to form a second plication. In other words, a first retractor 1014 can grasp tissue and form a first plication while a second retractor grasps other tissue and forms a second plication. Next, the two plications can be anchored together such that an open pocket 1104 is formed therebetween. In yet other embodiments, tissue graspers are introduced into the surgical site percutaneously for grasping tissue and manipulating it into adjacent plications that form the tube or open pocket 1104. In some embodiments, the tissue graspers pull tissue around the shaft 102 of the surgical device and position the tissue for implantation of the anchor object. Next, an anchor object is implanted to fasten the plications around the shaft of the surgical device. After the desired number of plications are fixed around the shaft of the surgical device, the end effecter 200 is straightened such as to be axially aligned with shaft 102 and the shaft 102 and end effecter 200 are removed through the open pocket 1104 of the tissue plications, leaving behind open pocket 1104, or as shown in FIGS. 12B and 12C artificial tissue tube 1250.

Figure 12A:
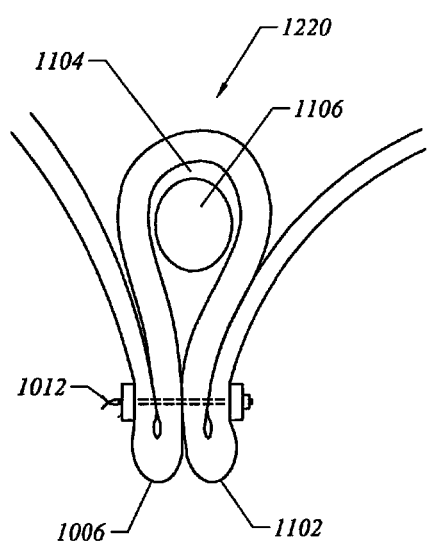
FIGS. 12A-12C show embodiments of a tissue plication and corresponding open tissue pocket according to embodiments of the present invention.
Figure 12B:
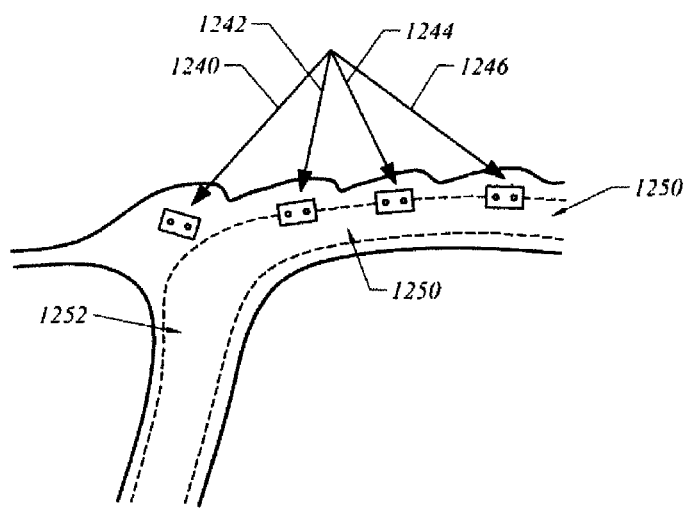

According to some embodiments, as shown in FIG. 12A, tissue 1220 that forms pocket 1104 between plications 1006 and 1102 may be tissue that requires treatment or can be used for locating a treatment. According to such embodiments, implant 1106 positioned in pocket 1104 is configured to treat tissue 1220 or otherwise provide treatment to surrounding areas. In other embodiments, tissue 1220 can be removed following the double plication procedure described with respect to FIGS. 10-12A. In other embodiments, tissue 1220 may dissolve or resorb following the double plication procedure.

Figure 12C:
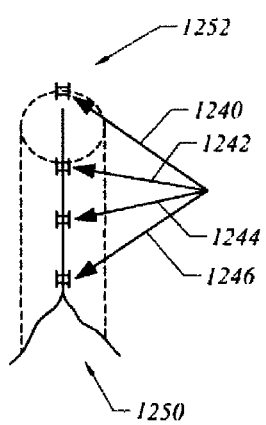

In other embodiments, multiple double plication procedures, such as the double plication procedure described with respect to FIGS. 10-12C can be performed on the same tissue, in the same organ, or the like. In some embodiments, as shown in FIGS. 12B-12C axially aligned double plications 1240, 1242, 1244, and 1246 can be positioned adjacent to each other such that each open pocket 1104, formed between the plications 1006 and 1102, is generally aligned and forms an artificial biological tube 1250. In some embodiments, artificial biological tube 1250 is formed by drawing each double plication together. In some embodiments, each plication 1240, 1242, 1244, and/or 1246 can be drawn together using surgical glue, suture material, surgical wire, staples, scoring the tissue such that the tissue reforms together, combinations thereof, or the like.

In some embodiments, vertically aligned double plications 1240, 1242, and 1244 are positioned, beginning at or distally near the gastro-esophageal-junction (GEJ) 1252 and extend into the stomach, thereby forming an artificial GEJ or gastric tube 1250. In some embodiments, when the artificial gastric tube is flaccid, i.e., empty, the artificial gastric tube acts as a gastric flap or valve for protecting the esophagus from gastric fluids. Thus, the formation of such an artificial gastric tube can be a treatment for gastro-esophageal reflux disorder (GERD). In other embodiments, the formation of an artificial gastric tube can be a technique for gastric reconstruction or reduction surgery. According to such embodiments, the formation of such an artificial gastric tube effectively reduces the volume of the stomach of a patient, and thereby, stimulates the stomach into providing a sense of satiety with consumption of a smaller amount of food. According to some embodiments, between 1 and about 10 plications are positioned adjacent each other to form artificial tube 1250. In other embodiments, between 1 and about 8 plications are positioned adjacent each other to form artificial tube 1250. In yet other embodiments, between 1 and about 5 plications are positioned adjacent each other to form artificial tube 1250. In yet other embodiments, between 1 and about 3 plications are positioned adjacent each other to form artificial tube 1250. In still other embodiments, a single plication is positioned adjacent the GEJ to form artificial tube 1250 or GERD treatment. According to other embodiments, between about 5 and about 8 plications are positioned adjacent each other to form artificial tube 1250. According to some embodiments, when artificial tube 1250 is formed with between one and two tissue plications, artificial tube 1250 is about 1 cm in length. In other embodiments, when artificial tube 1250 includes between about 10 to about 20 tissue plications, artificial tube 1250 is about 10 cm in length. In some embodiments, the diameter of artificial tube 1250 is between about 0.2 cm and about 10 cm. In other embodiments, the diameter of artificial tube 1250 is between about 0.5 cm and about 5 cm. In some embodiments, the diameter of artificial tube 1250 is between about 0.5 cm and about 3 cm. In some embodiments, the diameter of artificial tube 1250 is between about 0.5 cm and about 2 cm.

Figure 13A:
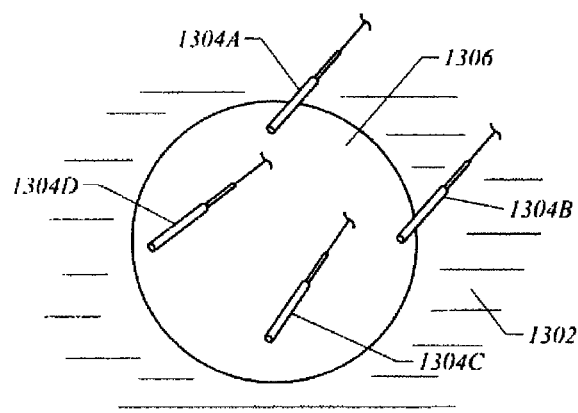
FIGS. 13A and 13B show implanted devices according to other embodiments of the present invention.
Figure 13B:
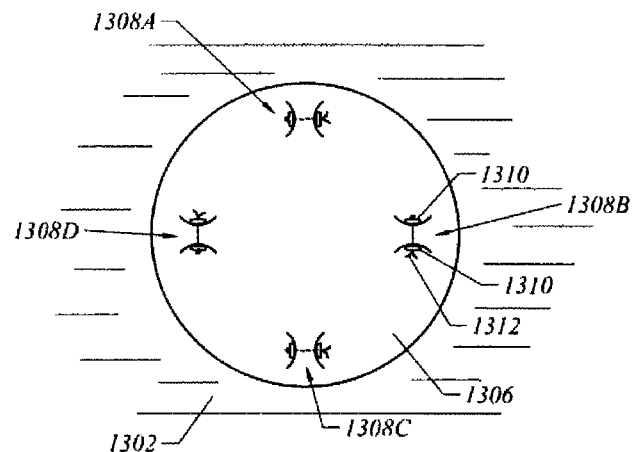

According to another embodiment, an implant device 1306 can be implanted onto tissue 1302 with multiple attachments, as shown in FIGS. 13A and 13B. According to some embodiments as shown in FIG. 13A, an implant 1306 can be located or held in position by coupling retractors 1304A-1304D to tissue 1302 and/or implant device 1306. In some embodiments, as shown in FIG. 13B, implant 1306 may be such a shape or dimension that multiple anchor implants are required for proper or secure attachment of implant 1306 to tissue 1302. As shown in FIG. 13B, multiple anchors 1308A-1308D are implanted through tissue 1302 and implant 1306 to affix implant 1306 as desired to tissue 1302. According to some embodiments, anchors 1308A-1308D include pledgets 1310 and suture 1312. According to some embodiments, pledgets 1310 and suture 1312 can be fabricated in accord with and from the materials of other pledgets and sutures described herein and incorporated herein by reference.

Figure 14:
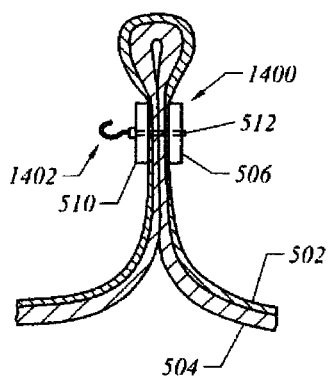
FIG. 14 shows an implanted device according to another embodiment of the present invention.

Referring now to FIG. 14, anchor implant 1400 includes a coupling 1402 and pledgets 506 and 510 coupled together by suture 512. Anchor implant 1400 is configured to couple tissue 502, 504 to itself or to an implanted device. According to some embodiments, coupling 1402 is configured to provide a site on anchor implant 1400 for attaching an implantable device, mechanical tool, drug eluding device, sensor, other device described or incorporated herein, combinations thereof, or the like. In some embodiments, coupling 1402 can be, but is not limited to a hook, clip, Velcro, magnet, loop, combinations thereof, or the like. According to some embodiments, coupling 1402 can be formed from a non-resorbable polymer, resorbable polymer, biodegradable polymer, drug eluding polymer, stainless steel, titanium, cobalt chromium, surgical material, combinations thereof, or the like.

Figure 17:
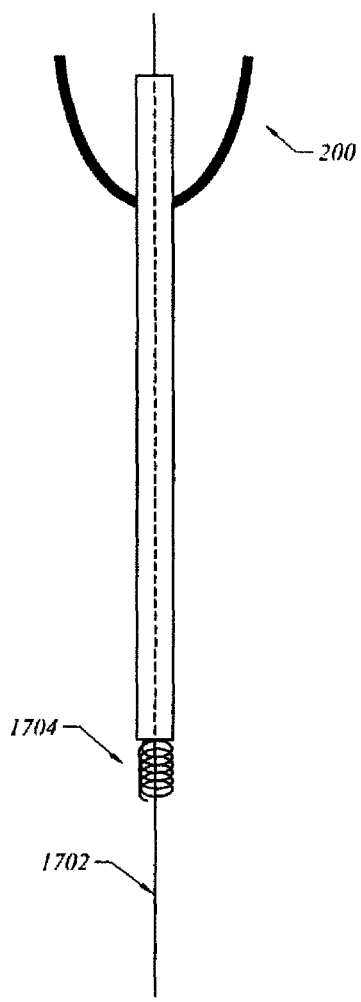
FIG. 17 shows a guide wire for guiding a tissue retractor according to an embodiment of the present invention.

According to another embodiment, as shown in FIG. 17, endoluminal surgical device 100 includes guide wire 1702 that includes tissue engaging retractor tip 1704. According to some embodiments, tissue engaging retractor tip 1704 is configured to releasable attach to tissue at a site near where an implant attachment site is targeted. In some embodiments, tissue engaging retractor tip 1704 can be, but is not limited to a corkscrew type design, screw threads, a hook, a loop, jaws, locking jaws, combinations thereof, and the like. In use, having a guide wire 1702 that can attach to tissue or target a tissue at or near an implant site can help direct where the implant device will pass and increases the efficiency and effectiveness of surgical procedures because the path that the device is require to pass is less rigorous and/or straighter.

Figure 15A:
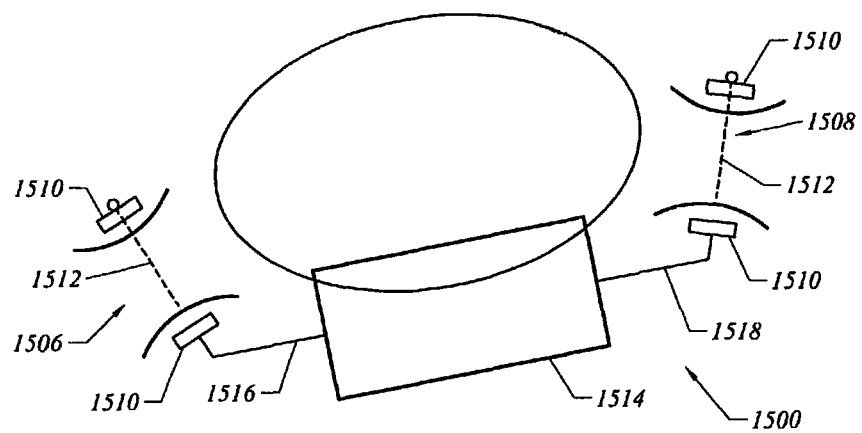
FIGS. 15A and 15B show an adjustable implantable device according to an embodiment of the present invention.
Figure 15B:
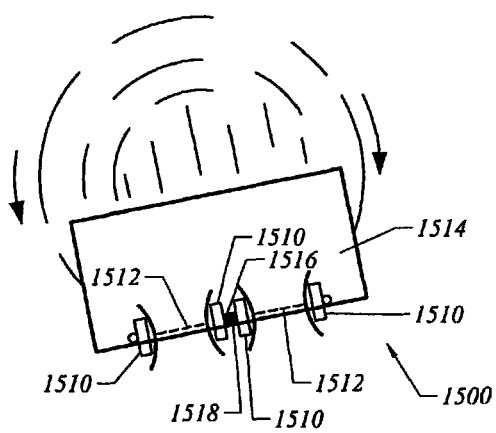

Referring now to FIGS. 15A and 15B, an adjustable implantable device 1500 is shown. In some embodiments, adjustable implantable device 1500 includes anchor implants 1506 and 1508, however, the number of anchor implants used in practice can vary to what is necessary for a particular procedure being performed, corrected, or desired. In some embodiments, anchor implants include pledgets 1510 connected by suture 1512. In some embodiments, anchor implant 1506 is coupled with adjustment mechanism 1514 by suture 1516 and anchor implant 1508 is coupled with adjustment mechanism 1514 by suture 1518. Adjustment mechanism 1514 is configured to adjust a physical parameter, such as for example, length, width, diameter, rotational axis, combinations thereof, or the like, in response to stimulation. In a preferred embodiment, adjustment mechanism 1514 linearly shortens in response to a predetermined stimulation. In some embodiments, a predetermined stimulation can be, but is not limited to, a radio frequency, ultra-sound, mechanical force, pressure, direct mechanical manipulation, magnetic force, chemical interaction, enzyme interaction, fluid, temperature, biological fluid, cellular interaction, cellular by-product, inter-cellular constituent, intra-cellular constituent, food, digestion by-product, time, combinations thereof, or the like.

In some embodiments, adjustable implant device 1500 is implanted into tissue 1504 surrounding gastro-esophageal-junction (GEJ) 1502. Having the adjustable implant device 1500 implanted in or near the GEJ 1502 allows the adjustable implant device 1500 to assist or augment the natural function of the GEJ 1502. According to an embodiment, in a relaxed state adjustable implant device 1500 leaves the GEJ 1502 in an open state such that food, liquids, or the like can be passed from the esophagus into the stomach of a patient. However, following activation, adjustable mechanism 1514 shortens and, thereby, tightens the GEJ 1502 such that gastric fluids are blocked from passing from the stomach into the esophagus and causing or worsening a patient's GERD condition. In some embodiments, adjustable mechanism 1514 can be a threaded mechanism, a coil mechanism, a spring mechanism, a magnetic mechanism, a ratchet mechanism, memory material, piezoelectric material, temperature sensitive material, combinations thereof, or the like.

In an alternative embodiment, adjustable implant device 1500 can be implanted in a stomach of a patient. Implanting adjustable implant device 1500 into a stomach allows a patient or physician to reversibly and/or temporarily restrict the volume of the stomach of a patient in response to a predetermined stimulus. According to some embodiments adjustable implant device 1500, when implanted in the stomach of a patient, can be retracted or adjusted prior to consuming food and thereby act as a temporary gastric restriction device. In some embodiments, adjustable implant device 1500 can be configured to respond to a digestive by-product, a cellular excretion, particular gastric fluids, an external stimulation, combinations thereof, or the like. It will be appreciated that adjustable implant device 1500 can be implanted in many locations in a patient, such as but not limited to, any sphincter, tubular organ such as the intestine, muscle, skeletal system, combinations thereof, or the like.

Figure 16:
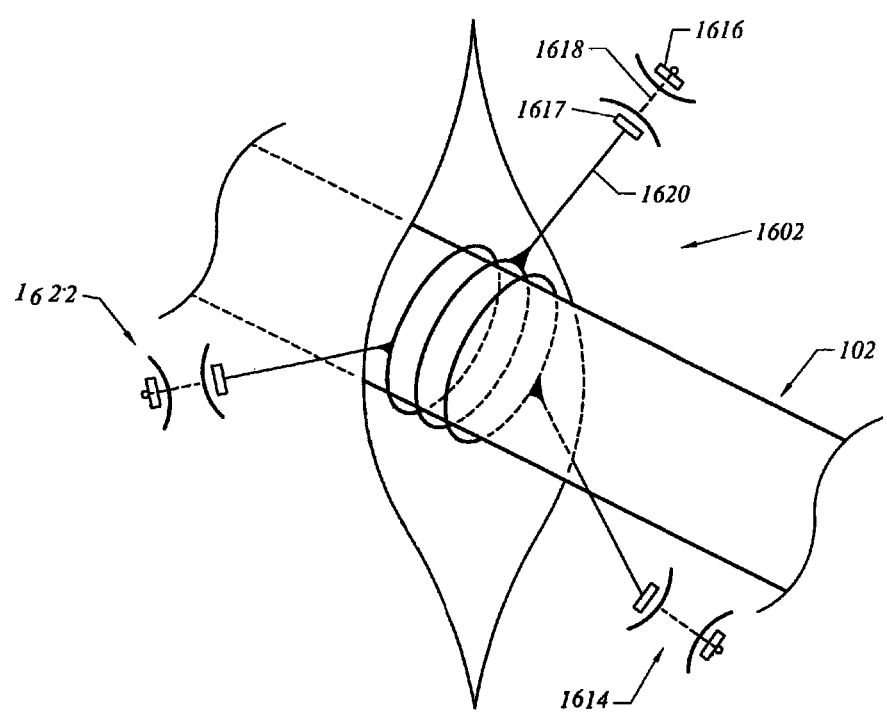
FIG. 16 shows a surgical device stabilization device according to an embodiment of the present invention.

Referring now to FIG. 16, a surgical stabilization system is shown. According to some surgical procedures a surgical device needs to be inserted through tissue, a tissue wall such as an abdominal wall, an organ wall such as the stomach, or the like. Often, when performing such surgical procedures a surgeon loses much control over a working end of a surgical instrument after the instrument has been passed through the tissue wall. According to an embodiment of the present invention, devices and mechanisms for improving surgical dexterity includes attaching stabilizers such as stabilizers 1606, 1614, and 1622 to tissue 1602 and shaft of implant device 102. According to alternative embodiments, more or less stabilizers can be utilized depending the requirements of a particular situation. For simplicity sake only one stabilizer will be described, however, it will be appreciated that each stabilizer includes generally the same construction. According to some embodiments, a stabilizer, such as stabilizer 1614 for example, includes a tissue anchor end and a device anchor end. The tissue anchor end includes pledgets 1616 and 1617 connected by suture material 1618. Pledgets 1616 and 1617 and suture material 1618 can be implanted according to methods and with devices disclosed herein or incorporated herein by reference. Pledget 1617 is further connected to line 1620 that extends from pledget 1617 to device 102. Line 1620 can be, but is not limited to, suture material, wire, rods, k-wires, t-bars, or other surgical material or devices that can support tension, pressure, and/or torque. According to some embodiments, the device anchoring end of stabilizer 1614 can be configured to couple to an attachment on device 102 such that a force applied to stabilizer 1614 can be translated to device 102 and/or manipulation force applied to device 102 can be leveraged over and around stabilizer 1614. It will be appreciated that stabilization devices can be implanted as desired to assist in manipulating surgical device 102.

What is claimed is:

1. An endoscopic treatment method, comprising:
   introducing an endoscopic device into a lumen of a patient without creating an incision in the patient;
   engaging a wall of the lumen with a tissue grasper;
   moving the wall of the lumen with the tissue grasper to position the wail of the lumen around a flexible shaft of the endoscopic device to form a plication in the wall of the lumen;
   anchoring the plication with an anchor object while the wall of the lumen is positioned around the shaft of the endoscopic device such that an open pocket is formed in the wall of the lumen;
   with the wall of the lumen positioned around the shaft of the endoscopic device and with the plication anchored with the anchor object, moving a second portion of the wall of the lumen to position the second portion of the wall around the shaft of the endoscopic device to form a second plication in the wall of the lumen;
   anchoring the second plication with a second anchor object such that a second open pocket is formed in the wall of the lumen; and
   removing the shaft from the open pockets, thereby leaving behind the open pockets, the plication anchored with the anchor object, and the second plication anchored with the second anchor object.

2. The method of claim 1, wherein the open pockets are aligned such that the open pockets form a hollow tube.

3. The method of claim 1, wherein moving the second portion of the wall of the lumen comprises moving the second portion with a second tissue grasper.

4. The method of claim 1, wherein the wall of the lumen remains positioned around the shaft of the endoscopic device and the second portion of the wall of the lumen remains positioned around the shaft of the endoscopic device when the second plication is anchored with the second anchor object.

5. The method of claim 2, wherein the shaft has a substantially cylindrical shape such that the hollow tube has a substantially cylindrical shape.

* * * * *